United States Patent [19]

Georgiev et al.

[11] Patent Number: 4,762,828

[45] Date of Patent: Aug. 9, 1988

[54] 1,2,4-TRIAZOLO[4,3-d]-4-AZATRICYCLO-[4.3.1.1$^{3,8}$]UNDECANE AND 3-SUBSTITUTED DERIVATIVES, AND INTERMEDIATES THEREOF

[75] Inventors: Vassil S. Georgiev, Penfield; Grace A. Bennett, Rochester, both of N.Y.

[73] Assignee: Pennwalt Corporation, Philadelphia, Pa.

[21] Appl. No.: 61,067

[22] Filed: Jun. 10, 1987

[51] Int. Cl.$^4$ .................... C07D 223/14; A61K 31/55
[52] U.S. Cl. .................... 514/214; 540/520; 540/578
[58] Field of Search ............... 540/520, 578; 514/214

[56] References Cited

U.S. PATENT DOCUMENTS 3,898,210 8/1975 Narayanan et al. ............. 514/214
4,557,865 12/1985 Georgiev et al. ............. 514/214

OTHER PUBLICATIONS

T. Sasaki et al., "Photochemical Synthesis of 4-Azahomoadamant-4-enes and Further Studies on their Reactivity in Some Cycloadditions", *J. Org. Chem.*, vol. 44, 3711–3715 (1979).

*Primary Examiner*—Robert T. Bond
*Attorney, Agent, or Firm*—Seidel, Gonda, Goldhammer & Abbott

[57] ABSTRACT

1,2,4-Triazolo[4,3-d]-4-azatricyclo[4.3.1.1$^{3,8}$]-undecane and 3-derivatives and intermediates thereof are described. The compounds are useful and antiinflammatory and antihypoxia agents.

11 Claims, No Drawings

1,2,4-TRIAZOLO[4,3-D]-4-AZATRICYCLO-[4.3.1.1³,⁸]UNDECANE AND 3-SUBSTITUTED DERIVATIVES, AND INTERMEDIATES THEREOF

BACKGROUND OF THE INVENTION

The invention relates generally to 1,2,4-triazolo[4,3-d]-4-azatricyclo[4.3.1.1$^{3,8}$]undecane and 3-substituted analogs thereof. These compounds possess anti-inflammatory activity as demonstrated by carrageenan-induced rat paw edema assay, and antihypoxia activity as determined by studies in mice.

U.S. Pat. No. 3,898,210 discloses 4-azatricyclo[4.3.1.1$^{3,8}$]undecane and 4-azatricyclo[4.3.1.1$^{3,8}$]undecan-5-one, and antiviral, cardiovascular, or anti-inflammatory N-substituted derivatives thereof. U.S. Pat. No. 4,557,865 discloses 5-substituted and/or N-substituted 4-azatricyclo[4.3.1.1$^{3,8}$]undecane and 4-azatricyclo[4.3.1.1$^{3,8}$]undecan-5-one compounds useful as antiviral agents.

T. Sasaki et al., *J. Org. Chem.*, Vol. 44, 3711–3715 (1979) discloses 1',3'-diphenyl-4-azahomoadamantano[4,5,-d]1',2',4'-$\Delta^{2'}$-triazoline and 1',3'-diphenyl-5-methyl-4-azahomoadamantano[4,5-d]-1',2',4'-$\Delta^{2'}$-triazoline.

None of the references teach the present invention.

SUMMARY OF THE INVENTION

The present invention provides a compound of the formula

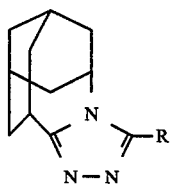

(1)

or a pharmaceutically acceptable acid addition salt thereof wherein R is hydrogen, lower alkoxy or halogen. The term "lower alkoxy" as used herein refers to an alkoxy group —OR' wherein R' is a straight or branched chain alkylene group having 1 to 4 carbon atoms.

Examples of suitable acids for forming the acid addition salts comprise inorganic acids such as hydrochloric, sulfuric, phosphoric, hydrobromic and hydroiodic acid, and organic acids such as fumaric, malic, acetic, lactic, citric and maleic acid.

The present invention further provides the novel intermediate of the formula

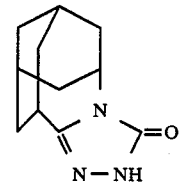

(2)

The invention also provides a method for treating a warm-blooded animal for inflammation or hypoxia which comprises administering to such animal an effective amount of a compound of formula 1.

DETAILED DESCRIPTION OF THE INVENTION 1,2,4-Triazolo[4,3-d]-4 azatricyclo[4.3.1.1$^{3,8}$]undecane (5) and 3-substituted derivatives thereof may be prepared from 5-methylthio-4-azatricyclo[4.3.1.1$^{3,8}$]undec4-ene hydroiodide (3) according to Scheme I.

Compound 3 may be prepared according to Example 6 of U.S. Pat. No. 4,557,865 "Substituted 4-Azatricyclo[4.3.1.1$^{3,8}$]undecane Compounds". Example 6 and the entire disclosure of U.S. Pat. No. 4,557,865 is incorporated herein by reference.

Compound 3 is condensed with formic acid hydrazide to form 1,2,4-triazolo[4,3-d]-4-azatricyclo[4.3.1.1$^{3,8}$]-undecane hydroiodide (4). Neutralization with sodium bicarbonate provides the free 1,2,4-triazolo[4,3-d]-4-azatricyclo[4.3.1.1$^{3,8}$]undecane (5). The latter may be treated with N-bromosuccinimide to produce the 3-bromo derivative, 3-bromo-1,2,4-triazolo[4,3-d]-4-azatricyclo[4.3.1.1$^{3,8}$]undecane (6), which is in turn coverted to the corresponding 3-alkoxy analog of formula 7 by reaction with R'OH, wherein R' is defined as above. When R'OH is ethanol, the compound 3-ethoxy-1,2,4-triazolo[4,3-d]-4-azatricyclo[4.3.1.1$^{3,8}$]undecane (10) results.

Scheme I

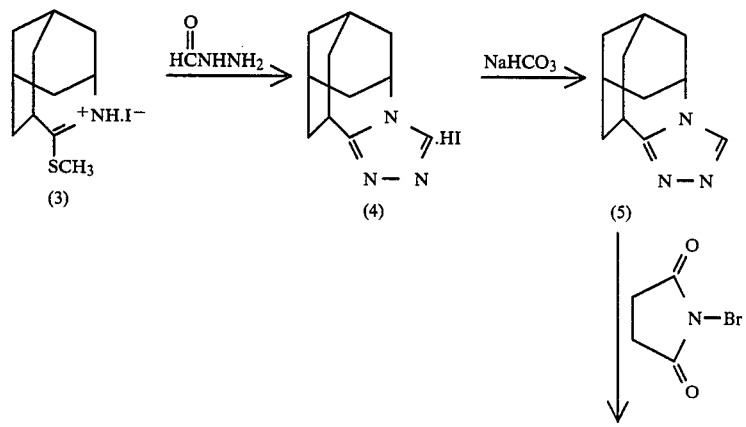

Scheme I

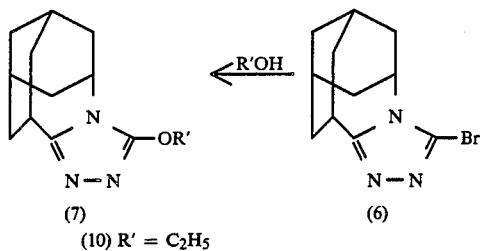

(10) R' = C₂H₅

Alternatively, the 1,2,4-triazolo[4,3-d]-4-azatricyclo[4.3.1.1³,⁸]undecane compounds of the invention may be prepared from 5-[(ethoxycarbonyl)hydrazonyl]-4-azatricyclo[4.3.1.1³,⁸]undecane hydroiodide according to Scheme II. The latter compound is neutralized with sodium bicarbonate. The resulting free base (8) is subjected to intramolecular cyclization in refluxing xylene to provide the novel intermediate 2,3-dihydro-3-oxo-1,2,4-triazolo[4,3-d]-4-azatricyclo[4.3.1.1³,⁸]undecane (2).

Compound 2 represents a novel heterocyclic system which is useful as an intermediate for the synthesis of the structurally-related anti-inflammatory and antihypoxic compounds of formula 1. Heterocyclic rings containing an amide group such as found in compound 2 may be converted to their corresponding imidoyl chloride analogs, such as compound 9. Brown et al., Eur. Pat. Appl. No. 39,920 (1981). Treatment of compount 9 with an appropriate alcohol, R'OH, (e.g. ethanol) will produce the 3-alkoxy substituted 1,2,4-triazolo[4,3-d]-4-azatricyclo[4.3.1.1³,⁸]undecane derivative of formula 7 wherein R' is as defined above.

Scheme II

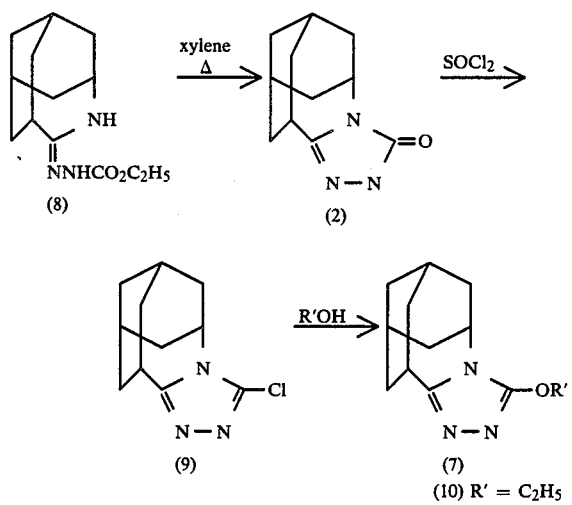

(10) R' = C₂H₅

The present invention will be illustrated in more detail by reference to the following non-limiting examples:

EXAMPLE 1

1,2,4-Triazolo[4,3-d]-4-azatricyclo[4.3.1.1³,⁸]undecane Hydroiodide (4)

A reaction mixture containing 5-methylthio-4-azatricyclo[4.3.1.1³,⁸]undec-4-ene hydroiodide (3) (0.5 g, 2.56 mmol), formic acid hydrazide (0.18 g, 3.0 mmol) in 50 ml toluene, was refluxed for 5 h. After cooling, the solid precipitate was filtered off and recrystallized from ethanol, leaving 0.23 g of compound 4. Mp 245–247° C.

Anal. Calcd. for $C_{11}H_{16}N_3I$: C, 41.66; H, 5.08; N, 13.25; I, 40.01. Found: C, 41.72; H, 5.15; N, 13.46; I, 39.79.

EXAMPLE 2

1,2,4-Triazolo[4,3-d]-4-azatricyclo[4.3.1.1³,⁸]undecane (5)

5 g of the hydroiodide salt compound 4 were dissolved in water and sodium bicarbonate was added portionwise until the pH of the solution reached 7. Then, the precipitate was extracted with methylene chloride. The organic extract was dried over $MgSO_4$, filtered and evaporated under reduced pressure to leave 2.35 g of 1,2,4-triazolo[4,3-d]-4-azatricyclo[4.3.1.1³,⁸]undecane (5) as white solid material which was recrystallized from ethyl acetate. Mp 112°–114° C.

Anal. Calcd. for $C_{11}H_{15}N_3$: C, 69.81; H, 7.99; N, 22.20. Found: C, 67.90; H, 7.98; N, 21.45.

EXAMPLE 3

3-Bromo-1,2,4-triazolo[4,3-d]-4-azatricyclo[4.3.1.1³,⁸]undecane (6)

A mixture of compound 5 (8.7 g, 10.045 mol) and N-bromosuccinimide (8.18 g, 0.045 mol) in 920 ml carbontetrachloride were refluxed, under nitrogen, for 2 h. Then, the reaction mixture was decanted and the solvent evaporated under reduced pressure leaving 7 g of crude compound 6, that was recrystallized from toluene. Mp 185°–186° C.

Anal. Calcd. for $C_{11}H_{14}BrN_3$, C, 49.27; H, 5.26; N, 15.67; Br, 29.80. Found: C, 48.86; H, 5.40; N, 15.41; Br, 29.90.

EXAMPLE 4

3-Ethoxy-1,2,4-triazolo[4,3-d]-4-azatricyclo[4.3.1.1³,⁸]undecane (10)

To a mixture of barium oxide (1.04 g, 6.8 mmol) in 6 ml of ethanol, was added dropwise a solution of compound 6 (0.175 g, 0.926 mmol) and copper(II) chloride (0.06 g, 0.432 mmol) in 4 ml dimethylformamide. The reaction mixture was refluxed for 24 h, then the solvent was evaporated under reduced pressure. The remaining solid residue was extracted with methanol and the insoluble material was filtered off. The filtrate was evaporated under reduced pressure leaving 0.071 g of compound 7. Mp 136°–138° C.

Anal Calcd. for $C_{13}H_{19}N_3O$: C, 66.92; H, 8.21; N, 18.01. Found: C, 66.67; H, 8.15; N, 18.00.

EXAMPLE 5

2,3-Dihydro-3-oxo-1,2,4-triazolo[4,3-d]-4-azatricyclo[4.3.1.1$^{3,8}$]undecane (2)

5-[(Ethoxycarbonyl)hydrazonyl]-4-azatricyclo[4.3.1.1$^{3,8}$]undecane hydroiodide (1.14 g, 3 mmol) is dissolved in 100 ml of water and sodium bicarbonate is added portionwise until the solution became neutral (pH7). Then the solution is extracted with methylene chloride, and the resulting organic extract is dried over magnesium sulfate and the solvent was removed under pressure. The residual 5-[(ethoxycarbonyl)hydrazonyl]-4-azatricyclo[4.3.1.1$^{3,8}$]undecane (8) is dissolved in 20 ml xylene and refluxed for 4 h. The solvent is evaporated under reduced pressure leaving compound 2 as a white solid which is recrystallized from ethyl acetate. Yield after recrystallization: 0.35 g. Mp 238°–240° C.

Anal. Calcd. for $C_{11}H_{15}N_3O$: C, 64.37; H, 7.37; N, 20.47. Found: C, 64.49; H, 7.52; N, 20.38.

The compounds of the invention possess anti-inflammatory activity as determined by the carrageenan-induced rat paw edema assay when administered orally. They also exhibit potent antihypoxia activity in mice when administered by intraperitoneal injection.

The antihypoxia activity of 1,2,4-triazolo[4,3-d]-4-azatricyclo[4.3.1.1$^{3,8}$]undecane (5) is summarized in Table 1.

TABLE 1

| Minimal Neurotoxic Dose (mg/kp, ip) | Estimated LD$_{50}$ (mg/kg, ip) | Antihypoxia Activity of 1,2,4-Triazolo-[4,3-d]-4-azatricyclo[4.3.1.1$^{3,8}$]undecane | | | | | | |
|---|---|---|---|---|---|---|---|---|
| | | Antihypoxia | | | | | | |
| | | Dose (mg/kg) | Route | N$^1$ | Temp. | Survival Minutes | | |
| | | | | | | Control | Compound | P |
| 6 | 12 | 6 | ip | 5 | 35° C. | 2.08 | 5.78 | =0.04 |
| | | 1 | iv | 5 | 35° C. | 2.36 | 2.34 | NS |
| | | 1.5 | iv | 5 | 35° C. | 2.30 | 3.02 | NS |

N$^1$ = Number of mice in each group
NS = Not significant, P >0.05
ip = intraperitoneal administration
iv = intravenous administration The antihypoxia test measures the survival duration of mice in a normobaric atmosphere consisting of 96% nitrogen and 4% oxygen, at 35° C. The mice are considered dead when they stop visible respiration. The test indicates potential clinical utility in situations of central nervous system hypoxia, such as occurs following stroke, cardiac arrest, and traumatic accidents.

As observed from Table 1, 1,2,4-triazolo[4,3-d]-4-azatricyclo[4.3.1.1$^{3,8}$]undecane (5), at a dose of 6 mg/kg (i.p.), prolonged by more than 2-fold the survival time of mice in the antihypoxia test. The quantity "P" in the Table denotes statistical significance.

Anti-inflamatory activity was determined by carrageenaninduced paw edema of laboratory rats. Groups of six male Sprague Dawley rats orally received compound suspended in a 1% aqueous solution of Methocel brand methylcellulose. Control rats received a 0.5% aqueous solution of Methocel only. Two hours later, each rat received a subcutaneous injection of 0.1 ml of a 1% homogenized suspension of carrageenan in the plantar surface of the right hind paw.

Immediately, the volume of the paw was measured by immersing it in mercury to above the lateral mateolus. The mercury in a glass cylinder 25 mm in diameter and 60 mm deep was connected at the bottom on the cylinder by a column of water to a Statham transducer (model P23BB), range 0–5 cm of mercury pressure. The volume was recorded electronically on a Beckman recorder, R511. Three hours later, the inflamed paw volume was measured again, and the change in volume was recorded for each group. Indomethacin, a known anti-inflamatory agent, was included as a standard.

The compounds of Examples 1 and 2 demonstrated activity in the assay, as shown in Table 2.

TABLE 2

| Ex. No. | Dose (mg/kg) | % Inhibition | |
|---|---|---|---|
| control | — | 63.9% | Edema |
| Indomethacin | 4.0 | 52.8% | |
| 1 | 25.0 | 17.0% | |
| 1 | 50.0 | 43.4% | |
| 1 | 100.0 | 56.6.% | |
| 2 | 25.0 | 17.0% | |
| 2 | 50.0 | 28.3% | |
| 2 | 100.0 | —% | |

The present invention may be embodied in other specific forms without departing from the spirit or essential attributes thereof and, accordingly, reference should be made to the appended claims, rather than to the foregoing specification, as indicating the scope of the invention.

We claim:

1. A compound having the formula:

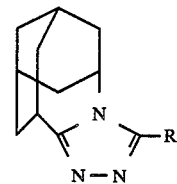

(1)

or a pharmaceutically acceptable acid addition salt thereof wherein R is selected from the group of hydrogen, lower alkoxy and halogen.

2. A compound according to claim 1, wherein R is hydrogen.

3. A compound according to claim 1, wherein R is bromine.

4. A compound according to claim 1 wherein R is chlorine.

5. A compound according to claim 1 wherein R is ethoxy.

6. The hydoiodide addition salt of the compound according to claim 2.

7. A process for treating a warm-blooded animal for inflamation or hypoxia which comprises administering to such animal an effective amount of the compound of claim 1.

8. A process according to claim 7 wherein the compound is 1,2,4-triazolo[4,3-d]-4-azatricyclo[4.3.1-1³,⁸]undecane or an addition salt thereof.
9. A process according to claim 8 wherein the compound is 1,2,4-triazolo[4,3-d]-4-azatricyclo[4.3.1-1³,⁸]undecane.
10. A process according to claim 8 wherein the compound is a hydroiodide addition salt.
11. The compound of the formula:
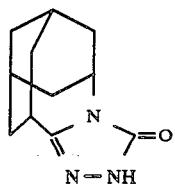
(2)
* * * * *